United States Patent [19]

Li

[11] Patent Number: 5,449,366

[45] Date of Patent: Sep. 12, 1995

[54] LAPAROSCOPIC NEEDLE HOLDER

[75] Inventor: Lehmann K. Li, Wellesley, Mass.

[73] Assignee: Li Medical Technologies, Inc., Shelton, Conn.

[21] Appl. No.: 245,252

[22] Filed: May 17, 1994

Related U.S. Application Data

[63] Continuation of Ser. No. 877,546, May 1, 1992, abandoned.

[51] Int. Cl.⁶ .............................................. A61B 17/00
[52] U.S. Cl. .................................... 606/147; 606/207
[58] Field of Search .................. 606/1, 108, 127, 128, 606/139, 144, 145, 147, 148, 205-211, 222; 128/750-755; 294/3.6, 19.1

[56] References Cited

U.S. PATENT DOCUMENTS

| | | | |
|---|---|---|---|
| 857,824 | 6/1907 | McNeal | 606/147 |
| 1,539,221 | 5/1925 | Tennant | |
| 2,363,334 | 11/1944 | Jones | 606/147 |
| 3,877,434 | 4/1975 | Ferguson et al. | 606/148 |
| 3,995,619 | 12/1976 | Glatzer | |
| 4,576,162 | 3/1986 | McCorkle | 128/785 |
| 4,597,390 | 7/1986 | Mulhollan et al. | 606/148 |
| 5,015,250 | 5/1991 | Foster | 606/148 |

Primary Examiner—Stephen C. Pellegrino
Assistant Examiner—William Lewis
Attorney, Agent, or Firm—Pandiscio & Pandiscio

[57] ABSTRACT

A laparoscopic needle holder comprising a longitudinally extending outer sheath and a longitudinally extending inner rod. The inner rod terminates in a generally J-shaped hook sized to grapple a curved surgical needle. The inner rod is adapted to be reciprocally received within the outer sheath such that the J-shaped hook can be moved between (1) a first position wherein the end of the hook's return is positioned relative to the forward end surface of the outer sheath so that a curved surgical needle can be grappled by the hook; (2) a second position wherein the end of the hook's return is positioned relative to the forward end surface of the outer sheath so that a curved surgical needle grappled by the hook will be slidably captured to the outer sheath; and (3) a third position wherein the end of the hook's return is positioned relative to the forward end surface of the outer sheath so that a curved surgical needle captured by the hook is prevented from rolling out of a preselected plane either toward or away from the sheath. Elements are also provided for selectively moving the sheath and the rod among the first, second and third relative positions, and for severing suture carried by an end of the curved surgical needle adjacent to the surgical site.

30 Claims, 5 Drawing Sheets

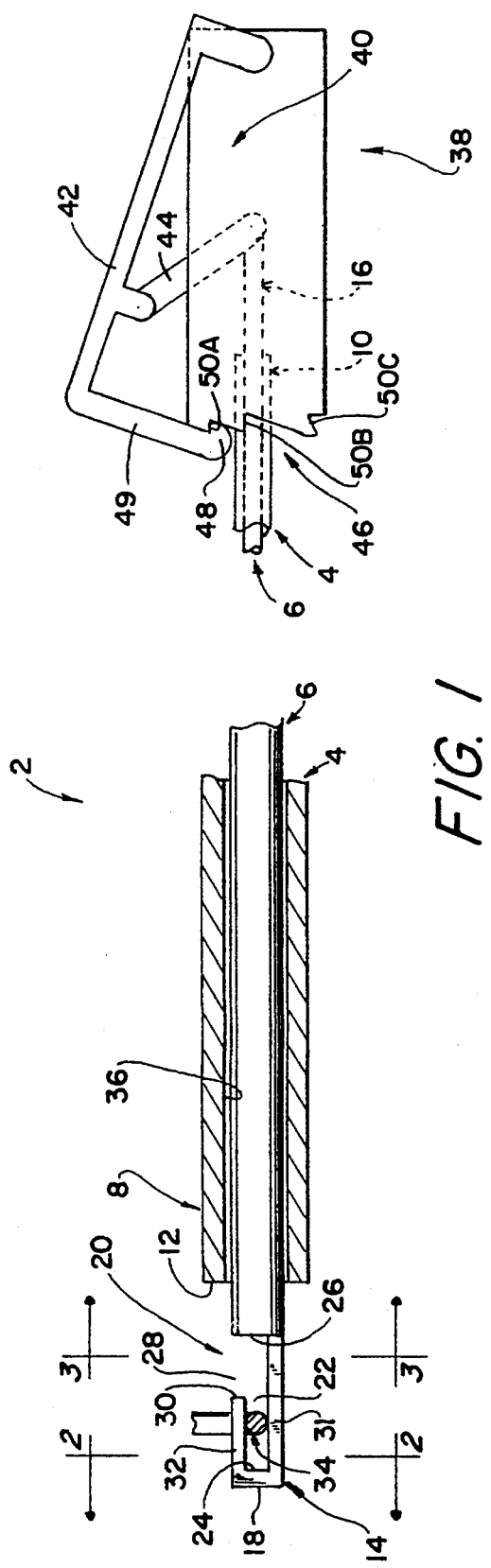
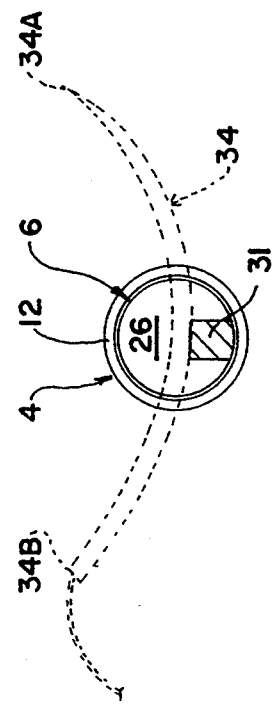
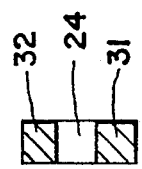
FIG. 1
FIG. 2
FIG. 3

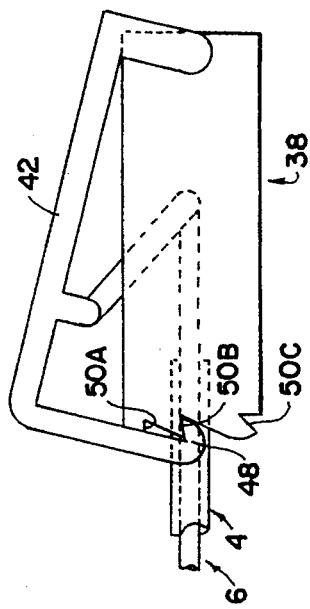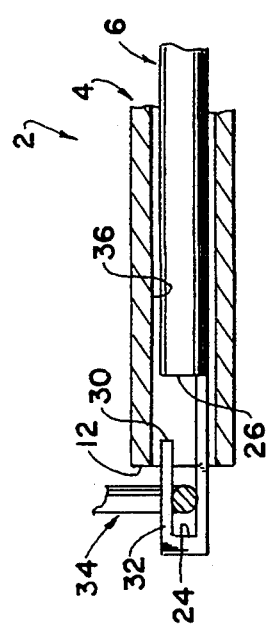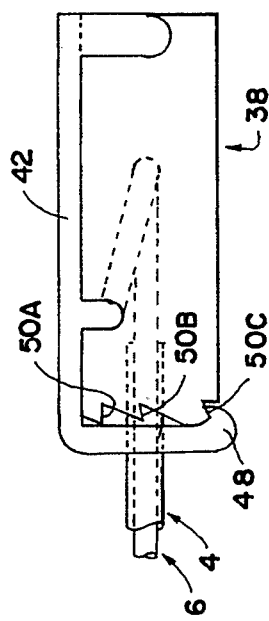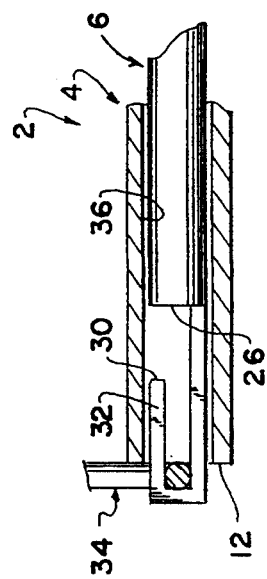
FIG. 4
FIG. 5

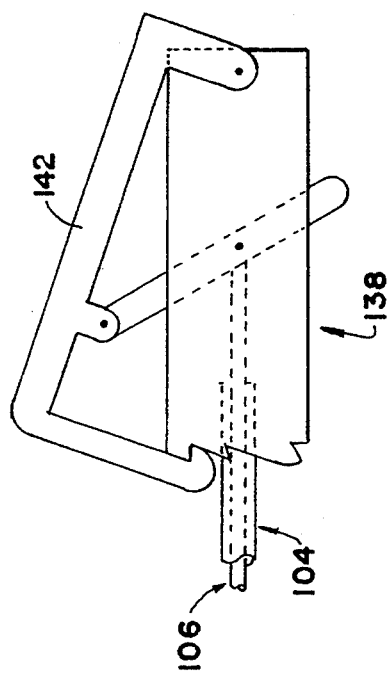
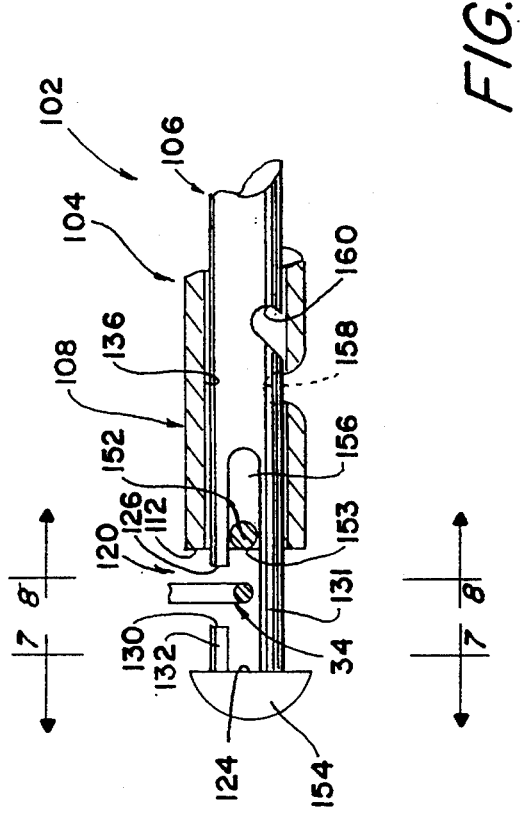
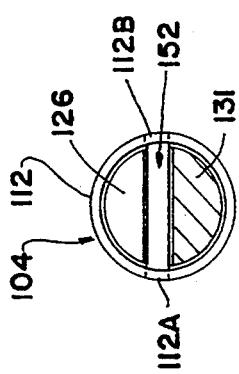
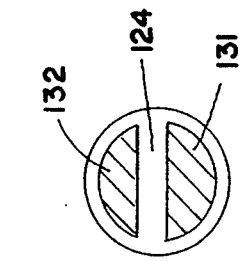
FIG. 6
FIG. 7
FIG. 8

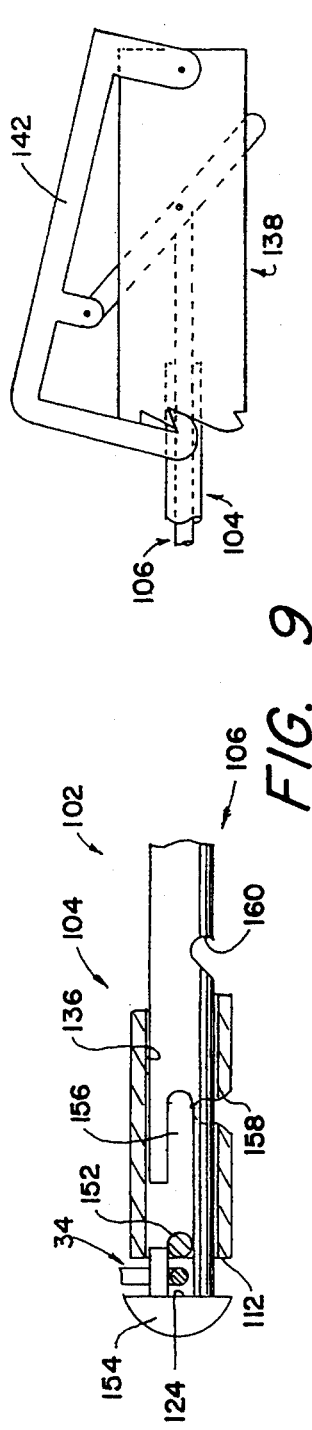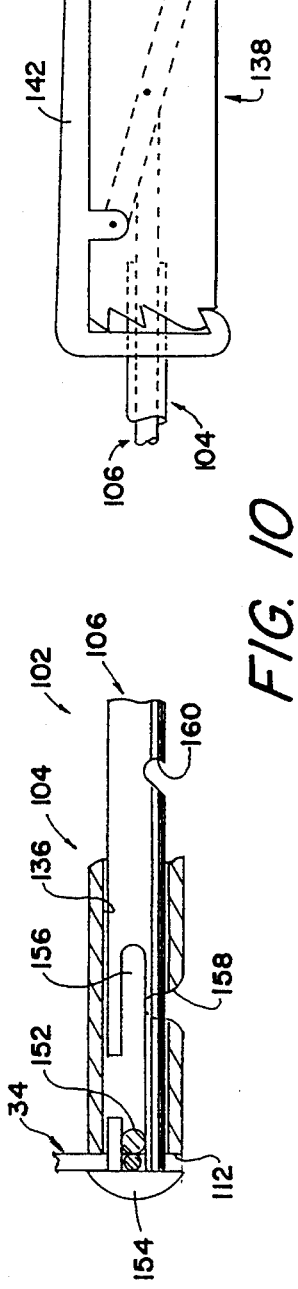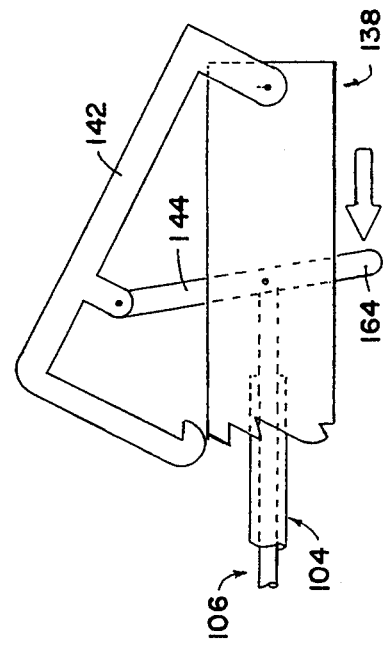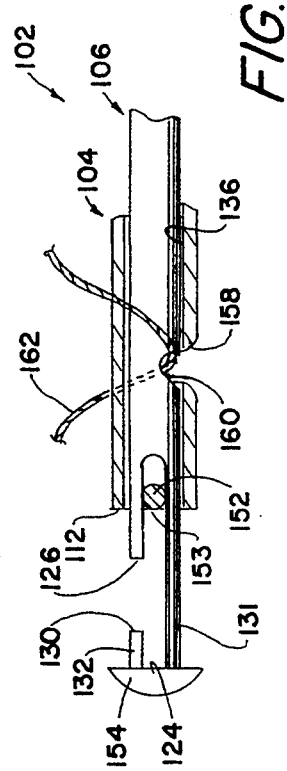
FIG. 9
FIG. 10
FIG. 11

LAPAROSCOPIC NEEDLE HOLDER

This is a continuation of application Ser. No. 07/877,546 filed on May 1, 1992, now abandoned.

FIELD OF THE INVENTION

This invention relates to laparoscopic surgery in general, and more particularly to needle holders for use in suturing tissue inside the body during such surgery.

BACKGROUND OF THE INVENTION

In laparoscopic surgery, access is gained to an interior surgical site by making one or more short incisions in the body which extend down to the interior surgical site, and then inserting a hollow tube or cannula into each incision so that the cannulas can act as liners to hold the incisions open and thereby provide portals leading down to the interior surgical site. A laparoscopic procedure can then be performed by passing instruments (e.g. cutting devices, clamps, viewing apparatus, etc.) down the cannulas so that the distal working ends of the instruments can be positioned and used about the surgical site, while the proximal handle ends of the instruments remain outside the body where they can be manipulated by the surgeon.

Laparoscopic procedures frequently involve the repair and/or removal of tissue from the interior surgical site, and often require that some sort of closure be made to the tissue being operated upon. Such closure can be effected through the use of conventional needles and suture, surgical clips or staples, or other known closure means. In this respect, it has been found that the use of conventional needles and suture can have significant advantages in many laparoscopic procedures, since they generally allow the tension of the closure to be dynamically adjusted during suture deployment. At the same time, however, the use of conventional needles and suture can also present significant difficulties in laparoscopic surgery, on account of the limited access provided to, and at, the interior surgical site.

One aspect of using conventional needles and suture which can be particularly troublesome in a laparoscopic surgical setting is that of engaging and gripping the needles at the interior surgical site. Currently, surgeons typically use long forceps-type needle holders to reach into the interior surgical site and engage and grip the needle during suturing. Unfortunately, while such a needle holder may be adequate in conventional surgical settings where there is generally fairly direct physical and visual access to the surgical site, it tends to be less effective in laparoscopic surgical settings due to the remote nature of the surgical site, the limited cannula access provided to that site, and the limited space available at the surgical site.

In addition to the foregoing, conventional forceps-type needle holders tend to provide relatively little tactile feedback to the surgeon. As a result, the surgeon has no reliable way of gauging, and hence of varying, the degree of engagement between the forceps and the needle. In other words, due to the relatively little tactile feedback provided by forceps-type needle holders, the surgeon has difficulty reliably engaging the needle with anything other than a totally fixed engagement.

Furthermore, inasmuch as forceps-type needle holders use an opposing jaw design, there tends to be no way to slidably capture the needle to the needle holder during use; the needle is either securely captured by the needle holder or it is not captured at all by the needle holder.

Even more important than the foregoing, however, is the problem of needle rolling during suturing. More specifically, the surgical needles employed during laparoscopic surgery generally tend to be curved needles, and it is important that they be held securely by the needle holder during use so that the plane of the needle always remains substantially perpendicular to the longitudinal axis of the needle holder; this orientation allows the surgeon to effect suturing with a simple rotational movement of the wrist. Any rolling of the needle relative to the suture holder during suturing will cause the plane of the needle to shift away from the desired perpendicular position and thereby inhibit the preferred suturing motion. Unfortunately, however, with the opposing jaw design of conventional forceps-type needle holders, where the jaws open and close with a vertical motion, the flat jaws of the needle holder engage the curved needle in a top-bottom sort of engagement which is applied against the curvature of the needle's arc. As a result, only a limited engagement can be achieved between the needle holder and needle. This tends to allow the curved needle to roll relative to the needle holder. Stated another way, since conventional forceps-type needle holders grasp the needle with a top-bottom engagement against the curvature of the needle's arc, rather than with a front-back sort of engagement parallel to the plane of the curved needle, no stabilizing vertical surfaces are available to lock the needle against rolling during use. As a result, the needle can shift away from the desired perpendicular position during use and thereby inhibit the desired suturing motion.

OBJECTS OF THE INVENTION

Accordingly, one object of the present invention is to provide a novel device for engaging and gripping a curved needle inside the body during a laparoscopic surgical procedure.

Another object of the present invention is to provide a novel method for engaging and gripping a curved surgical needle inside the body.

Another object of the present invention is to provide a novel way to engage and grip a curved needle inside the body during laparoscopic surgery.

And another object of the present invention is to provide a novel device for engaging and gripping a curved needle at a remote location within the body, wherein the device is capable of alternatively engaging the needle so as to hold it fast to the device or engaging the needle so that it can slip in a controlled manner relative to the device.

Another object of the present invention is to provide a novel device for engaging and gripping a curved needle at a remote location within the body, wherein the device is capable of engaging the needle so that the device can slip in a controlled manner along the arcuate length of the needle, or the needle can slip in a rolling sense relative to the device so that the direction of the needle point can be reversed relative to the device, all without completely releasing the needle from the needle holder.

Still another object of the present invention is to provide a needle holder capable of gripping a curved needle so as to prevent any needle rotation during use.

Yet another object of the present invention is to provide a needle holder of the sort adapted to hold a curved needle so that the plane of the needle always remains substantially perpendicular to the longitudinal axis of the needle holder during use, whereby the surgeon can effect suturing with a simple rotational movement of the wrist.

And another object of the present invention is to provide a needle holder capable of capturing a curved needle between opposing planar surfaces so that the plane of the needle is aligned with those opposing planar surfaces.

Another object of the present invention is to provide a needle holder adapted to engage a curved needle with a flat-to-flat, vise-like engagement along a sufficient portion of the needle's arc to prevent needle rolling relative to the holder.

Still another object of the present invention is to provide a holder adapted to grip a long, thin curved object and hold it fast so that the plane of the object extends perpendicular to the principal longitudinal axis of the holder.

Yet another object of the present invention is to provide a novel device for cutting suture at a remote location within the body.

And another object of the present invention is to provide a needle holder which can grapple a curved needle which is oriented in a direction other than perpendicular to the longitudinal axis of the needle holder and which can fixedly capture that needle to the needle holder, wherein in the process of fixedly capturing the needle to the needle holder, the needle holder will automatically reorient the needle so that the plane of the needle extends substantially perpendicular to the longitudinal axis of the needle holder.

And another object of the invention is to provide a needle holder which can first grapple and thereafter slidably capture a suture to the needle holder, wherein the suture has a needle attached to it, in order that the surgeon can slide the suture relative to the needle holder so as to introduce the needle into the needle holder where it can be fixedly captured to the needle holder.

SUMMARY OF THE INVENTION

These and other objects are achieved through the present invention, which comprises a needle holder comprising a longitudinally extending outer sheath and a longitudinally extending inner rod. The longitudinally extending outer sheath comprises a distal portion and a proximal portion, wherein the distal portion terminates in a distal end surface and defines a longitudinal bore which opens on the distal end surface and extends toward the sheath's proximal portion. The outer sheath's distal end surface is set substantially perpendicular to the longitudinal axis of the outer sheath. The inner rod comprises a distal portion and a proximal portion, wherein the distal portion terminates in a generally J-shaped hook sized to grapple a needle of the sort which is to be gripped by the device, and further wherein the inner rod is adapted to be received within the bore of the outer sheath and reciprocate relative to the outer sheath so that the J-shaped hook can be moved between:

(i) a first position wherein the end of the hook's return is spaced from the distal end surface of the outer sheath by a distance which is more than the thickness of the needle which is to be gripped, whereby the needle can be grappled by the hook;

(ii) a second position wherein the end of the hook's return is spaced from the distal end surface of the outer sheath by a distance which is less than the thickness of the needle, or is positioned within the bore of the outer sheath, but the interior surface at the base of the hook is spaced from the distal end surface of the outer sheath by a distance which is more than the thickness of the needle which is to be gripped, whereby a needle grappled by the hook will be slidably captured to the outer sheath; and (iii) a third position wherein the end of the hook's return is positioned within the bore of the outer sheath and the interior surface at the base of the hook is spaced from the distal end surface of the outer sheath by a distance which is substantially the same as the thickness of the needle which is to be gripped, whereby a needle grappled by the hook will be fixedly captured to the outer sheath.

The inner rod is formed so that the interior surface at the base of the hook is set substantially perpendicular to the longitudinal axis of the inner rod.

The outer sheath is sized, relative to the needle, such that its distal end surface can make a sufficient stabilizing contact with a needle held by the holder when the holder is in its aforementioned third position so as to prohibit any rolling of the two free ends of the curved needle toward the outer sheath. At the same time, the inner rod is sized relative to the needle, such that the interior surface at the base of the hook can make a substantially planar contact with a curved needle held by the holder when the holder is in its aforementioned third position so as to prohibit any rolling of the two free ends of the curved needle away from the outer sheath.

In addition to the foregoing, the outer sheath and inner rod are sized, relative to one another and to the needle, such that the needle holder can slip in a controlled manner along the arcuate length of the curved needle, without releasing the needle, when the holder is in its aforementioned second position; and the needle can slip in a rolling manner relative to the holder, without being released by the holder, so that the direction of the needle point can be reversed relative to the holder, when the holder is in its aforementioned second position.

The needle holder is used as follows. First, the needle holder is passed through a cannula down to the surgical site so that the distal end of the needle holder is positioned adjacent the curved needle which is to be engaged and gripped. Next, the needle holder is positioned in its aforementioned first position so that its hook is ready to grapple the needle. Then the needle holder is moved toward the needle so that the hook can grapple the needle. Next, the needle holder is positioned in its aforementioned second position so that the needle will be slidably captured to the outer sheath. This allows the needle holder to be moved about relative to the needle, or the needle to be moved about relative to the needle holder, without the needle holder completely releasing the needle. Finally, the needle holder is positioned in its aforementioned third position so that the needle will be fixedly captured to the outer sheath so that the plane of the needle extends substantially perpendicular to the longitudinal axis of the needle holder, and so that the needle will be locked against any rolling movement relative to the needle holder. The needle holder can then be used to move the needle about as required to effect suturing, and in particular can be used to effect suturing using the conventional wrist motion preferred by many surgeons.

BRIEF DESCRIPTION OF THE DRAWINGS

Still other objects and features of the present invention will be more fully disclosed or rendered obvious by the following detailed description of the present invention, which is to be considered together with the accompanying drawings wherein like numbers refer to like parts and further wherein:

FIG. 1 is a side view in elevation, partially in section, showing a needle holder formed in accordance with the present invention, wherein the needle holder is shown in its aforementioned first position;

FIG. 2 is a sectional view taken along line 2—2 of FIG. 1;

FIG. 3 is a sectional view taken along line 3—3 of FIG. 1, with a representative curved surgical needle being shown in phantom;

FIG. 4 is a side view in elevation, partially in section, showing the same needle holder shown in FIG. 1, except that the needle holder is shown in its aforementioned second position;

FIG. 5 is a side view in elevation, partially in section, showing the same needle holder shown in FIGS. 1 and 4, except that the needle holder is shown in its aforementioned third position;

FIG. 6 is a side view in elevation, partially in section, showing another needle holder formed in accordance with the present invention, wherein the needle holder is shown in its aforementioned first position;

FIG. 7 is a sectional view taken along line 7—7 of FIG. 6;

FIG. 8 is a sectional view taken along line 8—8 of FIG. 6;

FIG. 9 is a side view in elevation, partially in section, showing the same needle holder shown in FIG. 6, except that the needle holder is shown in its aforementioned second position;

FIG. 10 is a side view in elevation, partially in section, showing the same needle holder shown in FIGS. 6 and 9, except that the needle holder is shown in its aforementioned third position;

FIG. 11 is a side view in elevation, partially in section, showing the same needle holder shown in FIGS. 6, 9, and 10, except that the needle holder is shown in a fourth position;

DETAILED DESCRIPTION OF THE INVENTION

Figure 13:
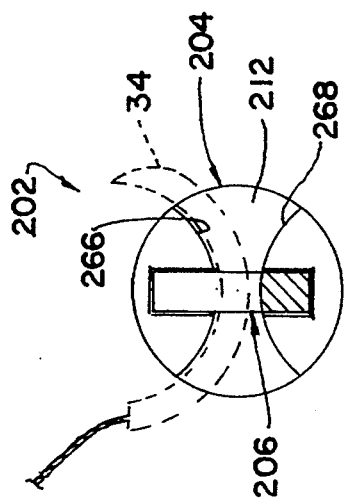
FIG. 13 is a sectional view taken along line 12—12 of FIG. 12.

Looking first at FIGS. 1-5, there is shown a needle holder 2 formed in accordance with the present invention. Needle holder 2 generally comprises an outer sheath 4 and an inner rod 6.

Outer sheath 4 comprises a distal portion 8 and a proximal portion 10. Outer sheath 4 terminates in a distal end surface 12 which is set substantially perpendicular to the longitudinal axis of outer sheath 4.

Inner rod 6 comprises a distal portion 14 and a proximal portion 16. Inner rod 6 terminates in a distal end surface 18.

The distal portion 14 of inner rod 6 includes a J-shaped hook 20 which is disposed slightly proximal to the rod's distal end surface 18. More particularly, the distal portion 14 of inner rod 6 includes a longitudinally extending slot 22 terminating in a distal end surface 24 and a proximal end surface 26, and a radially extending slot 28 defined by a distal end surface 30 and the aforementioned proximal end surface 26. Distal end surface 24 is set substantially perpendicular to the longitudinal axis of inner rod 6. The longitudinally extending slot 22 and radially extending slot 28 intersect one another as shown so as to form the J-hook 20. Hook 20 thus comprises an extender 31 and a return 32 terminating in the end surface 30. By forming hook 20 in the foregoing manner, it will be appreciated that inner rod 6 will have an outer diameter in the vicinity of hook 20 which is the same as the outer diameter along the remainder of the rod.

By way of further characterization, the radially extending slot 28 can be considered to be the "mouth" of hook 20, the portion of longitudinally extending slot 22 located between end surface 24 and end surface 30 can be considered to be the "interior" of hook 20, and the end surface 24 can be considered to be the "base" of hook 20, or the "interior surface at the base of hook" 20.

Inner rod 6 is formed so that the mouth of hook 20 (i.e., the distance between distal side surface 30 and proximal end surface 26) is substantially larger than the diameter of a curved surgical needle 34 which is to be engaged by the needle holder, the interior of hook 20 (i.e., the distance between end surface 24 and end surface 30) is substantially longer than the diameter of surgical needle 34, and the interior width of hook 20 (i.e., the width of longitudinally extending slot 22 between extender 31 and return 32) is slightly larger than the diameter of surgical needle 34, in order that the inner rod's hook 20 will be able to grapple a surgical needle 34 in the manner hereinafter described in further detail.

Outer sheath 4 and inner rod 6 are also formed so that the inner rod can make a close sliding fit within the interior bore 36 of the outer sheath.

On account of the foregoing construction, when inner rod 6 is positioned within outer sheath 4, the outer sheath and the inner rod can be moved relative to one another so as to assume:

(i) a first position (FIG. 1) wherein the end 30 of the hook's return 32 is spaced from the distal end surface 12 of outer sheath 4 by a distance which is more than the thickness of the surgical needle 34 which is to be gripped, whereby the needle can be grappled by hook 20;

(ii) a second position (FIG. 4) wherein the end 30 of the hook's return 32 is spaced from the distal end surface 12 of outer sheath 4 by a distance which is less than the thickness of the surgical needle 34, or is positioned within the bore 36 of outer sheath 4, but the interior surface 24 at the base of hook 20 is spaced from the distal end surface 12 of outer sheath 4 by a distance which is more than the thickness of the surgical needle, whereby a needle grappled by the hook will be slidably captured to the outer sheath; and (iii) a third position (FIG. 5) wherein the end 30 of the hook's return 32 is positioned within the bore 36 of outer sheath 4, and the interior surface 24 at the base of hook 20 is spaced from the distal end surface 12 of outer sheath 4 by a distance which is substantially the same as the thickness of the needle 34, whereby a needle grappled by the hook will be fixedly captured to the outer sheath.

Outer sheath 4 is sized, relative to needle 34, such that its distal end surface 12 can make a sufficient stabilizing contact with a needle 34 held by holder 2 when the holder is in its aforementioned third position (FIG. 5) so as to prohibit any rolling of the two free ends of needle 34 toward outer sheath 4. At the same timer inner rod 6 is sized, relative to needle 34, such that the interior surface 24 at the base of hook 20 can make a substantially planar contact with a needle held by holder 2 when the holder is in its aforementioned third position (FIG. 5) so as to prohibit any rolling of the two free ends of needle 34 away from outer sheath 4.

In addition to the foregoing, outer sheath 4 and inner rod 6 are also sized, relative to one another and to needle 34, such that needle holder 2 can slip in a controlled manner along the arcuate length of needle 34, without releasing the needle, when holder 2 is in its aforementioned second position (FIG. 4). Furthermore, needle 34 can slip in a rolling manner relative to holder 2, without being released by the holder, so that the direction of the needle point can be reversed relative to the holder, when the holder is in its aforementioned second position (FIG. 4). More specifically, needle 34 will be able to slip in rolling manner within hook 20 so that the location of the needle's two free ends 34A, 34B (FIG. 3) can be reversed from facing up to facing down, or from facing down to facing up (when viewed from the angle of view of FIG. 3).

A handle 38 is provided to move outer sheath 4 and inner rod 6 relative to one another so as to place the needle holder 2 into its aforementioned first, second and third positions. In this respect, it will be appreciated that such movement of outer sheath 4 and inner rod 6 relative to one another may be achieved by holding outer sheath 4 fixed in place and moving inner rod 6 back and forth relative to the outer sheath, or by holding inner rod 6 fixed in place and moving outer sheath 4 back and forth relative to the inner rod, or by moving both outer sheath 4 and inner rod 6 back and forth relative to one another.

In the preferred embodiment, the telescoping of outer sheath 4 and inner rod 6 relative to one another is achieved by holding outer sheath 4 fixed in place and moving inner rod 6 back and forth relative to the sheath. To this end, inner rod 6 is formed slightly longer than outer sheath 4, the proximal portion 10 of outer sheath 6 is fixed to handle 38, and handle 38 includes actuating means 40 which engage the distal portion 16 of inner rod 6 and urge the inner rod to move back and forth relative to the outer sheath when the surgeon manipulates actuating means 40. In the preferred embodiment, actuating means 40 comprises a thumb-operated lever 42 which is pivotally connected to the distal portion 16 of inner rod 6 by a connecting member 44, whereby counterclockwise motion of lever 42 (as seen from the angle of view of FIGS. 1, 4 and 5) will move inner rod 6 proximally relative to outer sheath 4. While not shown in the drawings, lever 42 is spring loaded so as to bias lever 42 in a clockwise direction (when seen from the angle of view of FIG. 1).

If preferred, a locking mechanism may be provided on handle 38 to hold outer sheath 4 and inner rod 6 releasably locked in certain predetermined positions. By way of example, such a locking mechanism might comprise the locking mechanism 46 shown in FIGS. 1, 4 and 5, wherein the locking mechanism comprises a latch 48 formed on the "free" end 49 of lever 42, and a plurality of detents 50A, 50B, 50C formed on the distal end of handle 38, whereby engagement of latch 48 with detents 50A, 50B, and 50C will releasably lock needle holder 2 in its first position (FIG. 1), second position (FIG. 4) and third position (FIG. 5), respectively. Of course, with such an arrangement, it will be necessary to make at least a portion of the "free" end 49 of lever 42 somewhat flexible so as to allow latch 48 to move about detents 50A, 50B and 50C. Other equivalent locking mechanisms of the sort well known in the art may alternatively be used.

Needle holder 2 is intended to be used as follows. First it is positioned in its aforementioned third position (FIG. 5) so that its hook 20 is substantially withdrawn into the distal end of sheath 4. This will keep hook 20 from inadvertently engaging any objects the hook may pass close to during cannula insertion. Then the distal end of needle holder 2 is passed through a cannula down to the surgical site and positioned close to the needle which is to be engaged and gripped.

Next, lever 42 is manipulated so as to put the needle holder into its aforementioned first position (FIG. 1). In this position, the holder's hook 20 is fully exposed and can be used to grapple and thereby engage a needle 34 located at the remote interior site.

Once needle 34 has been successfully grappled by hook 20, lever 42 is manipulated so as to put the needle holder into its aforementioned second position (FIG. 4). In this position, the inner rod's hook 20 will cooperate with the outer sheath's distal end surface 12 to slidingly capture needle 34 to needle holder 2. With the needle thus slidingly captured to the needle holder, the relative positioning of the needle and needle holder may be safely adjusted without fear that the needle will slip free from the needle holder. Such an arrangement is of significant advantage when dealing with a needle which is disposed at a remote surgical site, such as is generally the case in laparoscopic surgery. For example, with the needle thus slidingly captured to the needle holder, needle holder 2 can be slipped in a controlled manner along the arcuate length of needle 34, without releasing the needle from its grasp, so as to adjust the point at which holder 2 engages needle 34. In addition, when the needle is slidingly captured to the needle holder in the manner shown in FIG. 4, needle 34 can also be slipped in a rolling manner relative to holder 2, without being released by the holder, so that the direction of the needle point can be reversed relative to the holder. In other words, when the needle holder 2 is engaging a needle 34 in the manner shown in FIG. 4, if the needle is initially oriented so that its point is oriented in an upward direction (as defined by the angle of view of FIG. 4), it may be rolled within hook 20 so that it thereafter faces in a downward direction (as defined by the angle of view of FIG. 4); and if the needle is initially oriented in a downward direction (as defined by the angle of view of FIG. 4), it may be rotated within hook 20 so that it thereafter faces in an upward direction (as defined by the angle of view of FIG. 4).

Once needle 34 has been properly positioned relative to needle holder 2, lever 42 is manipulated again so as to put the needle holder into its aforementioned third position (FIG. 5). In this position, the inner rod's hook 20 will cooperate with the outer sheath's distal end surface 12 to fixedly capture needle 34 to needle holder 2. More specifically, as lever 42 is actuated so as to put needle holder 2 into its aforementioned third position (FIG. 5), inner rod 6 will move rearward relative to outer sheath 4. This action will bring the interior surface 24 at the base of hook 20 and the distal end surface 12 of outer sheath 4 together, in a parallel vice-like manner, so as to lock needle 34 securely in position relative to needle holder 2, with the plane of the needle extending substantially perpendicular to the longitudinal axis of needle holder 2. No rolling of needle 34 relative to holder 2 is permitted, since the sheath's distal end surface 12 is adapted to prohibit any rolling of the two free ends of needle 34 toward outer sheath 4, and the rod's interior surface 24 is adapted to prohibit any rolling of the two free ends of needle 34 away from outer sheath 4. Needle holder 2 can then be used to manipulate needle 34 as required to effect suturing at the surgical site.

For example, in a typical suturing operation, the needle holder 2 would engage the curved needle 34 adjacent its heel end 34B and the needle holder would be used to push the needle's tip end 34A through the tissue to be sutured. Then the needle holder would release the needle's heel end 34B, would engage and grip the needle adjacent its tip end 34A, and then pull the needle completely through the tissue. This process may be repeated as needed to effect the desired suturing.

It is to be appreciated that, on account of the unique construction of the present invention, needle holder 2 can grapple a needle 34 which is oriented in a direction other than perpendicular to the longitudinal axis of the needle holder 2, yet will automatically reorient the needle via its two vice-like surfaces 24 and 12 as the holder is put into its aforementioned third position, so that the plane of the needle thereafter extends substantially perpendicular to the longitudinal axis of the needle holder. Such a feature can be of significant importance in reducing the time needed to properly load the needle into the needle holder.

It is also to be appreciated that, on account of its unique construction, needle holder 2 can be used to first grapple a piece of suture attached to a surgical needle, and then slidably capture the suture to the needle holder, in order that the surgeon can thereafter slide the suture relative to the installation tool so as to conveniently present the needle to the needle holder, whereupon the needle holder can be further manipulated so as to fixedly capture the needle to the needle holder. Such a feature is of significant importance in laparoscopic procedures, where limited visibility and access can make finding and gripping the needle difficult.

Looking next at FIGS. 6-11, there is shown a needle holder 102 which is substantially identical to the needle holder 2 previously described, except as will hereinafter be described in detail.

More particularly, needle holder 102 has the distal end of its outer sheath 104, and the distal end of its inner rod 106, modified somewhat from that previously described so as to further improve the nature of the engagement of the needle 34 by the needle holder. To this end, outer sheath 104 has a cross member 152 extending across its inner bore 136 adjacent the outer sheath's distal portion 108. Cross member 152 may have a round cross-section, or more preferably it has either a square cross-section or a flattened-off round cross-section such that its distal-most edge 153 extends substantially parallel to the outer sheath's distal end surface 112. Cross member 152 is positioned so that its distal-most edge 153 is aligned with the outer sheath's distal end surface 112. As a result of this construction, cross member 152 provides a diametrically-extending seating surface 153 which extends between the two diametrically opposed portions 112A, 112B of the outer sheath's annular end surface 112. Surfaces 112A, 153 and 112B thereby provide a continuous planar surface which extends substantially perpendicular to the longitudinal axis of outer sheath 104, and against which a needle can rest when it is gripped by the needle holder, as will hereinafter be described in further detail.

Inner rod 106 has its distal tip enlarged so as to form a hemispherical cap 154. Cap 154, extender 131 and return 132 together form the hook 120, with return 132 terminating in end surface 130 and cap surface 124 defining the interior base of hook 120. Thus, cap surface 124 also provides a diametrically-extending flat seating surface which extends substantially perpendicular to the longitudinal axis of inner rod 106, and against which a needle can rest when it is gripped by the needle holder.

In addition to the foregoing, inner rod 106 also includes a longitudinal slot 156 which extends proximally from the inner rod's end surface 126. Slot 156 accommodates cross member 152 as inner rod 106 moves back and forth relative to outer sheath 104.

Needle holder 102 is used to engage and grip a needle 34 in the same way that needle holder 2 is used to engage and grip a needle. More specifically, needle holder 102 is first put into its aforementioned third position (FIG. 10) so that its hook 120 is substantially withdrawn into the distal end of sheath 104. This will prevent hook 120 from accidentally engaging any objects during cannula insertion. Then the distal end of needle holder 102 is passed through a cannula down to the interior surgical site and positioned close to the needle which is to be engaged and gripped. Then lever 142 of handle 138 is manipulated so as to put the needle holder into its aforementioned first position (FIG. 6), so that the holder's hook 120 is fully exposed and ready to grapple a needle 34 at the surgical site. Next the holder's handle 138 is manipulated by the surgeon so that the holder's distal end grapples a needle 34 at the surgical site. Once this case been done, lever 142 is manipulated again so as to put needle holder 102 into its aforementioned second position (FIG. 9), so that needle 34 is slidably captured to needle holder 102. This allows the surgeon to thereafter adjust the relative positioning of the needle and needle holder without fear that the needle will slip away from the needle holder. Again, this feature is of significant importance when dealing with a curved needle located at a remote surgical site, as is generally the case with laparoscopic surgery. Such adjustment might consist of slipping needle holder 102 in a controlled manner along the arcuate length of needle 34 so as to adjust the point at which needle holder 102 engages needle 34; and/or such adjustment might consist of rolling needle 34 over relative to needle holder 102 so as to reverse the direction of the needle point relative to holder 102, as discussed previously with respect to holder 2. Finally, lever 142 is manipulated once again so as to put needle holder 102 into its aforementioned third position (FIG. 10). In this position, the hemispherical cap's flat diametrical surface 124 will cooperate with the sheath's distal end surface portion 112A, the cross member's diametrical distal-most surface 153, and the sheath's distal end surface 112B so as to fixedly capture needle 34 to needle holder 102. More specifically, as lever 142 is actuated so as to put needle holder 102 into its aforementioned third position (FIG. 10), inner rod 106 will move rearward relative to outer sheath 104. This will bring the hemispherical cap's flat diametrical surface 124 at the base of hook 120 toward the flat planar surface formed by the sheath's distal end surface portion 112A, the cross member's diametrical distal-most surface 153, and the sheath's distal end surface 112B, in a parallel, vice-like manner, so as to lock needle 34 securely in position relative to needle holder 102, with the plane of the needle extending substantially perpendicular to the longitudinal axis of needle holder 102. No rolling of needle 34 relative to holder 2 is permitted, since the sheath's distal end surface portion 112A, the cross member's diametrical distal most surface 153, and the sheath's distal end surface 112B are adapted to prohibit any rolling of the two free ends of needle 34 toward sheath 104, and the rod's flat diametrical surface 124 is adapted to prohibit any rolling of the two free ends of needle 34 away from outer sheath 4. Needle holder 102 can then be used to manipulate needle 34 as required to effect suturing at the surgical site.

Still looking now at FIGS. 6 and 9-11, the needle holder 102 can also include suture cutting means for severing a length of suture at the interior surgical site. Such a feature can be desirable since it means that suture cutting can be effected quickly and easily at the conclusion of suturing without requiring the introduction of an additional tool to the remote surgical site. More specifically, needle holder 102 includes suture cutting means in the form of a first slot 158 formed in outer sheath 104 and a second slot 160 formed in inner rod 106. Slot 158 preferably extends substantially parallel to the sheath's distal end surface 112, and slot 160 preferably extends at an acute angle (e.g. at an approximately 45 degree angle) to the longitudinal axis of inner rod 106, as shown. Each of the slots 158 and 160 is sized so as to be able to accommodate a suture therein. The first and second slots 158 and 160 are capable of being aligned with one another when outer sheath 104 and inner rod 106 are in the position shown in FIG. 11 (hereinafter sometimes referred to as the needle holder's fourth position), wherein first slot 158 is sized so as to overlie second slot 160 in the manner shown in FIG. 11 when members 104 and 106 are in this position. However, outer sheath 104 and inner rod 106 are formed so that the first and second slots 158 and 160 will not be aligned with one another when the outer sheath and inner rod are in any other position, i.e., the first and second slots 158 and 160 will not be aligned with one another when the needle holder is in any of its aforementioned first position (FIG. 6), second position (FIG. 9) or third position (FIG. 10). As a result of this construction, when it is desired to sever a suture 162 (FIG. 11) at the conclusion of each suturing operation, the needle holder is placed in the position shown in FIG. 11 so that the first and second slots 158 and 160 are in alignment with one another, suture 162 is then slipped into the aligned slots 158 and 160, and lever 142 depressed so as to withdraw inner rod 106 relative to outer sheath 104. This will cause slot 160 to move out of alignment with slot 158, thereby causing inner rod 106 and outer sheath 104 to sever suture 162 by a shearing action. In order to facilitate placing needle holder 102 in its aforementioned fourth position (i.e., the position of FIG. 11), connecting member 144 may be extended somewhat at 164 so that it protrudes from the bottom of handle 138 and provides a means by which the surgeon may help urge the inner rod 106 into the desired position.

While not shown explicitly in the drawings, it is also to be appreciated that the inner rod's slot 160 is always protectively contained within outer sheath 104, except for when it is deliberately placed into alignment with the outer sheath's slot 158 for suture cutting, i.e., when the tool is in the position shown in FIG. 11. In all other positions, including the tool's aforementioned first position (FIG. 6), second position (FIG. 9) and third position (FIG. 10), the inner rod's slot 160 is safely encased within the outer sheath 104, and the outer sheath's own slot 158 is largely filled by the body of inner rod 106. As a result of this construction, there is little chance of tool 102 accidentally cutting any tissue while tool 102 is being inserted down to the surgical site, or while it is in, or is being manipulated between, its first position (FIG. 6), second position (FIG. 9) and/or third position (FIG. 10) during needle engagement and gripping.

Figure 12:
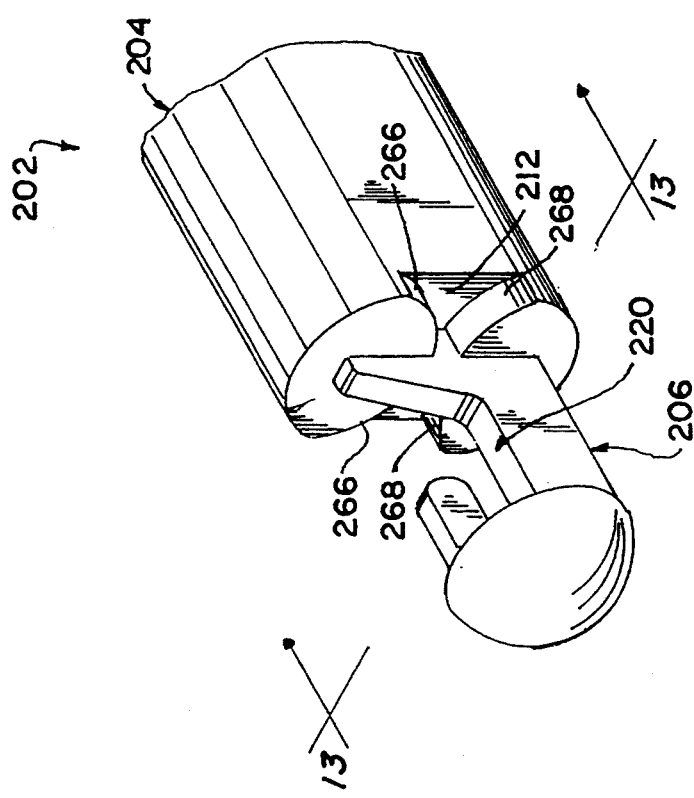
FIG. 12 is a perspective view showing yet another needle holder formed in accordance with the present invention.

It is also anticipated that one might modify the geometry of the outer sheath somewhat so as to provide improved surfaces for carrying needle 34. Thus, for example, FIGS. 12 and 13 show a needle holder 202 which comprises an outer sheath 204 having curved needle-bearing surfaces 266 and 268 disposed adjacent its flat needle-bearing surface 212. Curved needle-bearing surfaces 266 and 268 have a degree of curvature which is substantially the same as the degree of curvature of a standard curved surgical needle. As a result, when a needle 34 is disposed in hook 220 and inner rod 206 is moved rearward so as to clamp needle 34 against outer sheath 204, the curved needle 34 will be held flat against the sheath's flat needle-bearing surface 212 and either curved needle-bearing surface 266 or 268 (depending on whether the needle's two free ends are pointing upwardly or downwardly, respectively, as viewed from the angle of view of FIG. 13). Such a construction will help ensure that needle 34 will not move relative to needle holder 204 during suturing.

It is also to be appreciated that while the tools 2, 102 and 202 have been described in the context of engaging and gripping a curved surgical needle, they could also be used to engage any other long thin arcuately curved object which must be engaged and stabilized at a remote site. Thus, for example, tools 2, 102 and 104 might be used to engage and grip curved pieces of hypodermic (or larger) tubing, pieces of curved wire, long thin curved prosthetic devices, etc.

Numerous modifications may also be made to the apparatus and method disclosed above without departing from the scope of the present invention. Thus, for example, an alternative handle arrangement of the sort well known in the art could be provided for moving the outer sheath and inner rod back and forth relative to one another.

These and other changes of their type are believed to be obvious to a person skilled in the art, and are considered to be within the scope of the present invention.

What is claimed is:

1. A device for manipulating a curved, elongated surgical needle having a length of suture attached thereto, said device comprising:
   a shaft, means for cutting said suture, and hook means;
   said shaft having a longitudinal axis, a distal end disposed in a plane normal to said longitudinal axis, and at least one longitudinal opening extending into said distal end of said shaft; and
   said hook means:
   (a) extending outwardly from said opening in proximity to said distal end;

(b) being sized to contain a significant portion of the length and the transverse cross-section of said curved, elongated surgical needle, and including a closed end and an open end, said open end being sized for the passage of said transverse cross-section of said curved, elongated surgical needle therethrough, and said closed end defining a planar surface disposed substantially parallel to said distal end of said shaft; and (c) being selectively reciprocally movable relative to said distal end between (1) a first position wherein said open end of said hook means is located in spaced relation to said distal end of said shaft so as to allow said transverse cross-section of said curved, elongated surgical needle to enter said hook means, (2) a second position wherein said open end of said hook means is at least partially closed by said distal end of said shaft so as to be smaller than said transverse cross-section of said curved, elongated surgical needle, and the aperture defined by said hook means and said distal end of said shaft has a transverse cross-section larger than said transverse cross-section of said curved, elongated surgical needle, and (3) a third position wherein the aperture defined by said hook means and said distal end of said shaft has a transverse cross-section substantially equal to the transverse cross-section of said curved, elongated surgical needle, and wherein said distal end of said shaft prevents the ends of said curved, elongated surgical needle from rotating toward said shaft and said planar surface prevents the ends of said curved, elongated surgical needle from rotating away from said shaft, when said significant portion of the length of said curved, elongated surgical needle is located in said aperture.

2. The device of claim 1 wherein said means for cutting said suture comprises a slot in said shaft adapted to receive a length of said suture and movable means within said shaft for severing said length of suture received in said slot.

3. A method for manipulating a curved, elongated object, said method comprising the steps of:

(i) providing a shaft and hook means;
said shaft having a longitudinal axis, a distal end disposed in a plane normal to said longitudinal axis, and at least one longitudinal opening extending into said distal end; and
said hook means:
(a) extending outwardly from said opening in proximity to said distal end of said shaft;
(b) being sized to contain a significant portion of the length and the transverse cross-section of said curved, elongated object, and including a closed end and an open end, said open end being sized for the passage of said transverse cross-section of said curved, elongated object therethrough, and said closed end defining a planar surface disposed substantially parallel to said distal end of said shaft; and
(c) being selectively reciprocally movable relative to said distal end between (1) a first position wherein said open end of said hook means is located in spaced relation to said distal end of said shaft so as to allow said transverse cross-section of said curved, elongated object to enter said hook means, (2) a second position wherein said open end of said hook means is at least partially closed by said distal end of said shaft so as to be smaller than said transverse cross-section of said curved, elongated object, and the aperture defined by said hook means and said distal end of said shaft has a transverse cross-section larger than the transverse cross-section of said curved, elongated object, and (3) a third position wherein the aperture defined by said hook means and said distal end of said shaft has a transverse cross-section substantially equal to the transverse cross-section of said curved, elongated object, and wherein said distal end of said shaft prevents the ends of said curved, elongated object from rotating toward said shaft, and said planar surface prevents the ends of said curved, elongated object from rotating away from said shaft when said significant portion of the length of said curved, elongated object is located in said aperture;

(ii) positioning the distal end of said shaft adjacent to said curved, elongated object;

(iii) positioning said device in said first position, and grappling said object with said hook means; and (iv) thereafter positioning said device in said third position so as to fixedly capture said curved, elongated object between said distal end of said shaft and said closed end of said hook means.

4. The method of claim 3 wherein after step (iii) but prior to step (iv) said device is positioned in its second position and manipulated so as to allow said curved elongated object to slidably move relative to said device to thereby place said curved, elongated object in a preselected spacial orientation relative to said device.

5. The method of claim 4 wherein said curved elongated object is a surgical needle having a length of suture attached thereto located at a surgical site adjacent a tissue mass and wherein said device is used to alternately insert said needle into and withdraw said needle from said tissue mass.

6. The method of claim 5 wherein said device further comprises means for severing said suture.

7. A method according to claim 3 further comprising means for selectively moving said shaft and said hook means among said first, second and third positions.

8. A method according to claim 7 wherein said means for selectively moving said shaft and said hook means comprises activation means connected to the proximal ends of said shaft and said hook means, said activation means being adapted to alternatively releasably lock said shaft and said hook means in either said first position, said second position or said third position.

9. A device for engaging a curved, elongated object, said device comprising:

a longitudinally-extending first member having a longitudinal axis and including a distal portion and a proximal portion wherein said distal portion terminates in a substantially planar distal surface disposed substantially normal to said longitudinal axis and defines a longitudinal bore which opens on said distal end surface and extends toward said proximal portion;

a longitudinally-extending rod including a distal portion and a proximal portion wherein said distal portion terminates in a substantially J-shaped hook portion sized to grapple a significant portion of the length of said curved, elongated object which is to be engaged by said device, said hook portion comprising an extender portion, a substantially planar base portion and a return portion which terminates in a hook end surface;

said rod being adapted to be received within said bore of said first member such that said substantially planar base portion is maintained substantially parallel to said distal end surface and such that said rod can be selectively reciprocated relative to said first member so that said J-shaped hook portion can move between:

(1) a first position wherein said hook end surface of said return portion is spaced from said distal end surface of said first member by a distance which is greater than said transverse cross-section of said curved, elongated object, whereby said significant portion of the length of said curved, elongated object can be grappled by said hook;

(2) a second position wherein said hook end surface of said return portion is spaced from said distal end surface of said first member by a distance which is less than said transverse cross-section of said curved, elongated object, but said substantially planar base portion of said hook is spaced from said distal end surface of said first member by a distance which is greater than said transverse cross-section of said curved, elongated object; and (3) a third position wherein said substantially planar base portion of said hook portion is spaced from said distal end surface of said first member by a distance which is substantially the same as said transverse cross-section of said curved, elongated object, and wherein said distal end surface of said first member prevents the ends of said curved, elongated object from rotating toward said first member, and said substantially planar base portion of said rod prevents the ends of said curved, elongated object from rotating away from said first member, when said significant portion of the length of said curved, elongated object is disposed between said distal end surface and said substantially planar base portion and said J-shaped hook portion is disposed in its said third position; and said device further comprising means for selectively moving said first member and said hook portion among said first, second and third positions, said means for moving said first member and said hook portion comprising activation means connected to the proximal ends of said first member and said hook portion, said activation means being adapted to alternatively releasably lock said first member and said hook portion in either said first position, said second position or said third position.

10. A method for engaging a curved, elongated object, said method comprising the steps of:

(a) providing a device comprising:

a longitudinally-extending first member having a longitudinal axis and including a distal portion and a proximal portion wherein said distal portion terminates in a substantially planar distal surface disposed substantially normal to said longitudinal axis and defines a longitudinal bore which opens on said distal end surface and extends toward said proximal portion;

a longitudinally-extending rod including a distal portion and a proximal portion wherein said distal portion terminates in a substantially J-shaped hook portion sized to grapple said curved, elongated object which is to be engaged by said device, said hook portion comprising an extender portion, a substantially planar base portion and a return portion which terminates in a hook end surface;

said rod being adapted to be received within said bore of said first member such that said substantially planar base portion is maintained substantially parallel to said distal end surface and such that said rod can be selectively reciprocated relative to said first member so that said J-shaped hook portion can move between:

(1) a first position wherein said hook end surface of said return portion is spaced from said distal end surface of said first member by a distance which is greater than the diameter of the transverse cross-section of said curved, elongated object, whereby said curved, elongated object can be grappled by said hook;

(2) a second position wherein said hook end surface of said return portion is spaced from said distal end surface of said first member by a distance which is less than the diameter of the transverse cross-section of said curved, elongated object, but the substantially planar base portion of said hook is spaced from said distal end surface of said first member by a distance which is more than the diameter of the transverse cross-section of said curved, elongated object; and (3) a third position wherein said substantially planar base portion of said hook portion is spaced from said distal end surface of said first member by a distance which is substantially the same as the diameter of the transverse cross-section of said curved, elongated object, and further wherein said distal end surface of said first member is adapted to prevent the ends of said curved, elongated object from rotating toward said first member, and said substantially planar base portion of said rod is adapted to prevent the ends of said curved, elongated object from rotating away from said first member, when said curved, elongated object is disposed between said distal end surface and said substantially planar base portion and said J-shaped hook portion is disposed in its said third position;

(b) positioning the distal end of said shaft adjacent to said curved, elongated object;

(c) positioning said device in said first position, and grappling said object with said hook means; and (d) thereafter positioning said device in said third position so as to fixedly capture said curved, elongated object between said distal end of said shaft and said closed end of said hook means.

11. The method of claim 10 wherein after step (c) but prior to step (d) said device is positioned in its second position and manipulated so as to allow said curved elongated object to slidably move relative to said device to thereby place said curved, elongated object in a preselected spacial orientation relative to said device.

12. The method of claim 11 wherein said curved elongated object is a surgical needle having a length of suture attached thereto located at a surgical site adjacent a tissue mass and wherein said device is used to alternately insert said needle into and withdraw said needle from said tissue mass.

13. The method of claim 12 wherein said device further comprises means for severing said suture.

14. A method according to claim 10 further comprising means for selectively moving said first member and said hook portion among said first, second and third positions.

15. A method according to claim 14 wherein said means for selectively moving said first member and said hook portion comprises activation means connected to the proximal ends of said first member and said hook portion, said activation means being adapted to alternatively releasably lock said first member and said hook portion in either said first position, said second position or said third position.

16. A device for manipulating a curved, elongated object having a length of suture affixed to one of its ends, said device comprising:
an elongate, hollow shaft, an elongate rod, activation means and means for severing said suture;
said elongate hollow shaft having a proximal end, a distal end, a longitudinal axis and a lumen extending therethrough from said proximal end to said distal end, and defining an annular, planar surface at said distal end disposed normally to said longitudinal axis; and
said elongated rod including a second distal end, a second proximal end and a second longitudinal axis, and defining a substantially J-shaped hook adjacent its said second distal end, said hook including a closed, substantially planar end portion disposed substantially normally to said second longitudinal axis and a substantially radially facing open end spaced proximally of said second distal end, said open end of said hook having a transverse cross-section at least as great as the transverse cross-section of said curved, elongate object, said closed end of said hook defining a volume sized to engage a significant portion of the length of said curved, elongate object, and said rod being disposed substantially co-axially within said elongate, hollow shaft for reciprocal movement with respect thereto;
whereby said rod and said shaft may be selectively moved relative to each other between positions such that (1) the open end of said hook is spaced from said distal end of said shaft so that the transverse cross-section and said significant portion of said length of said curved, elongated object may be grappled by said hook; (2) the open end of said hook is at least partially closed such that said curved, elongated object may be entrapped within said hook while allowing said curved, elongated object to move transversely relative to said hook; and (3) the open end of said hook is at least partially closed such that said significant portion of the length of said curved, elongated object may be captivated by said hook in a manner precluding transverse rotational movement of said curved, elongated object relative to said hook and said shaft; and
wherein said activation means are attached to the proximal end of said shaft and said second proximal end of said rod, said activation means being manipulatable so as to control the movement of said shaft and said rod relative to each other.

17. The device of claim 16 wherein said severing means comprises a first slot in said shaft located proximally of said distal end surface and sized to receive a length of said suture, and a slot in said rod located substantially further proximally of said second distal end than the distance of said first slot from said distal end surface of said shaft, said second slot being alignable with said first slot and sized to receive a length of suture, whereby said slots may be aligned so as to simultaneously receive a length of suture, and said length of suture may thereafter be severed by moving said shaft and said rod relative to one another.

18. A method for manipulating a curved, elongated object having a length of suture attached thereto, said method comprising the steps of:
(a) providing an elongate, hollow shaft and an elongate rod;
said elongate hollow shaft having a proximal end, a distal end, a longitudinal axis and a lumen extending therethrough from said proximal end to said distal end, and defining and annular, planar surface at said distal end disposed normally to said longitudinal axis; and
said elongated rod including a second distal end, a second proximal end and a second longitudinal axis, and defining a substantially J-shaped hook adjacent its said second distal end, said hook including a closed, substantially planar end portion disposed substantially normally to said second longitudinal axis and a substantially radially facing open end spaced proximally of said second distal end, said open end of said hook having a transverse cross-section at least as great as the transverse cross-section of said curved, elongated object, said closed end of said hook defining a volume sized to engage said significant portion of the length of said curved, elongate object, and said rod being disposed substantially co-axially within said elongate, hollow shaft for reciprocal movement with respect thereto;
whereby said rod and said shaft may be selectively moved relative to each other between positions such that (1) the open end of said hook is spaced from said distal end of said shaft so that the transverse cross-section and said significant portion of the length of said curved, elongated object may be grappled by said hook; (2) the open end of said hook is at least partially closed such that said curved, elongated object may be entrapped within said hook while allowing said curved, elongated object to move transversely relative to said hook; and (3) the open end of said hook is at least partially closed such that said significant portion of the length of said curved, elongated object may be captivated by said hook in a manner precluding transverse rotational movement of said curved, elongated object relative to said hook and said shaft;
(b) positioning the distal end of said shaft adjacent said curved, elongated object;
(c) positioning said rod and said shaft in said first position, and grappling said curved, elongated object with said hook means; and
(d) thereafter positioning said rod and said shaft in said third position so as to fixedly capture said curved, elongated object between said distal end of said shaft and said closed end of said hook means.

19. The method of claim 18 wherein after step (c) but prior to step (d) said device is positioned in its second position and manipulated so as to allow said curved elongated object to slidably move relative to said device to thereby place said curved, elongated object in a preselected spacial orientation relative to said device.

20. The method of claim 19 wherein said curved elongated object is a surgical needle having a length of suture attached thereto located at a surgical site adjacent a tissue mass and wherein said device is used to alternately insert said needle into and withdraw said needle from said tissue mass.

21. The method of claim 20 wherein said device further comprises means for severing said suture.

22. A method according to claim 18 further comprising means for selectively moving said shaft and said rod among said first, second and third positions.

23. A method for suturing a tissue mass utilizing an elongate, curved surgical needle having a length of suture attached thereto and located at a surgical site adjacent said tissue mass, said method comprising the steps of:
  (a) providing a device comprising:
    a longitudinally-extending first member having a longitudinal axis and including a distal portion and a proximal portion wherein said distal portion terminates in a substantially planar distal surface disposed substantially normal to said longitudinal axis and defines a longitudinal bore which opens on said distal end surface and extends toward said proximal portion;
    a longitudinally-extending rod including a distal portion and a proximal portion wherein said distal portion terminates in a substantially J-shaped hook portion sized to grapple a significant portion of the length of said elongate, curved surgical needle which is to be engaged by said device, said hook portion comprising an extender portion, a substantially planar base portion and a return portion which terminates in a hook end surface;
    said rod being adapted to be received within said bore of said first member such that said substantially planar base portion is maintained substantially parallel to said distal end surface and such that said rod can reciprocate relative to said first member so that said J-shaped hook portion can move between:
      (1) a first position wherein said hook end surface of said return portion is spaced from said distal end surface of said first member by a distance which is greater than the transverse cross-section of said elongate, curved surgical needle, whereby said significant portion of the length of said elongate, curved surgical needle can be grappled by said hook;
      (2) a second position wherein said hook end surface of said return portion is spaced from said distal end surface of said first member by a distance which is less than the transverse cross-section of said elongate, curved surgical needle, but the substantially planar base portion of said hook is spaced from said distal end surface of said first member by a distance which is greater than the transverse cross-section of said elongate, curved surgical needle grappled by said hook portion, whereby said elongate, curved surgical needle may be slidably captured to said first member; and
      (3) a third position wherein said substantially planar base portion of said hook portion is spaced from said distal end surface of said first member by a distance which is substantially the same as the transverse cross-section of said elongate, curved surgical needle, and wherein said distal end surface of said first member prevents said elongate, curved surgical needle from rotating toward said first member, and said substantially planar base portion of said rod prevents said elongate, curved surgical needle from rotating away from said first member, when said significant portion of the length of said elongate, curved surgical needle is disposed between said distal end surface and said substantially planar base portion and said J-shaped hook portion is disposed in its said third position, whereby an elongate, curved surgical needle grappled by said hook portion may be fixedly captured to said first member;
  (b) positioning the distal end of said shaft adjacent to said elongate, curved surgical needle;
  (c) positioning said device in said first position, and grappling said elongate, curved surgical needle with said hook means;
  (d) positioning said device in its second position, and manipulating said device so as to allow said elongate, curved surgical needle to slidably move relative to said device to thereby place said elongate, curved surgical needle in a preselected spacial orientation relative to said device;
  (e) thereafter positioning said device in said third position so as to fixedly capture said elongate, curved surgical needle between said distal end of said shaft and said closed end of said hook means; and
  (f) alternately inserting said needle into and withdrawing said needle from said tissue mass.

24. The method of claim 23 wherein said device further comprises means for severing said suture.

25. A device for manipulating a curved, elongated object having a length of suture affixed to one of its ends, said device comprising:
  an elongate, hollow shaft, an elongate rod, activation means and suture severing means;
  said elongate, hollow shaft having a proximal end, a distal end, a longitudinal axis and a lumen extending therethrough from said proximal end to said distal end, and defining planar surface at said distal end disposed normally to said longitudinal axis;
  said elongate rod including a second distal end, a second proximal end and a second longitudinal axis, and defining a substantially J-shaped hook adjacent its said second distal end, said hook including a closed, substantially planar end portion disposed substantially normally to said second longitudinal axis and a substantially radially facing open end spaced proximally of said second distal end, said open end of said hook having a transverse cross-section at least as great as the transverse cross-section of said object, said closed end of said hook defining a volume sized to engage a significant portion of the length of said curved, elongate object, and said rod being disposed substantially co-axially within said elongate, hollow shaft for reciprocal movement with respect thereto;

said activation means being connected to both said proximal end of said shaft and said second proximal end of said rod, and being manipulatable so as to control the movement of said shaft and said rod relative to each other; and said severing means being defined by a portion of said shaft and a portion of said rod, whereby said rod and said shaft may be selectively moved relative to each other between positions such that (1) the open end of said hook is spaced from said distal end of said shaft so that the transverse cross-section and said significant portion of the length of said curved, elongated object may be grappled by said hook; (2) the open end of said hook is at least partially closed by said distal end of said shaft such that said curved, elongated object may be entrapped within said hook while allowing said curved, elongated object to move transversely relative to said hook; and (3) the open end of said hook is at least partially closed such that said curved, elongated object may be entrapped within said hook in a manner precluding transverse movement of said curved, elongated object relative to said hook.

26. The device of claim 25 wherein said severing means comprises a first slot in said shaft located proximally of said distal end surface and sized to receive a length of said suture, and a slot in said rod located substantially further proximally of said second distal end than the distance of said first slot from distal end surface of said shaft, said second slot being alignable with said first slot and sized to receive a length of suture, whereby alignment of said slots to at the same time receive a length of suture followed by relative movement of said shaft and said rod severs said length of suture.

27. A method according to claim 22 wherein said means for selectively moving said shaft and said rod comprises activation means connected to the proximal ends of said shaft and said rod, said activation means being adapted to alternatively releasably lock said shaft and said rod in either said first position, said second position or said third position.

28. A device for manipulating a curved, elongated object, said device comprising:
a shaft and hook means;
said shaft having a longitudinal axis, a distal end disposed in a plane normal to said longitudinal axis, and at least one longitudinal opening extending into said distal end of said shaft; and
said hook means:
(a) extending outwardly from said opening in proximity to said distal end;
(b) being sized to contain a significant portion of the length and the transverse cross-section of said curved, elongated object, and including a closed end and an open end, said open end being sized for the passage of said transverse cross-section of said curved, elongated object therethrough, and said closed end defining a planar surface disposed substantially parallel to said distal end of said shaft; and
(c) being selectively reciprocally movable relative to said distal end between (1) a first position wherein said open end of said hook means is located in spaced relation to said distal end of said shaft so as to allow said transverse cross-section of said curved, elongated object to enter said hook means, (2) a second position wherein said open end of said hook means is at least partially closed by said distal end of said shaft so as to be smaller than said transverse cross-section of said curved, elongated object, and the aperture defined by said hook means and said distal end of said shaft has a transverse cross-section larger than said transverse cross-section of said curved, elongated object, and (3) a third position wherein the aperture defined by said hook means and said distal end of said shaft has a transverse cross-section substantially equal to the transverse cross-section of said curved, elongated object, and wherein said distal end of said shaft prevents the ends of said curved, elongated object from rotating toward said shaft and said planar surface prevents the ends of said curved, elongated object from rotating away from said shaft, when said significant portion of the length of said curved, elongated object is located in said aperture;

and further wherein said distal end of said shaft defines a first substantially planar surface adapted to receive longitudinally disposed portions of said hook means in said at least one longitudinal opening, and wherein said planar surface defined by said closed end of said hook means defines a second substantially planar surface substantially parallel to said first planar surface, said second planar surface carrying said longitudinally extending portions of said hook means in alignment with said longitudinal openings in said first planar surface, whereby when said transverse cross-section of said curved, elongated object is located in said hook means and said device is manipulated so as to place it in its third position, said first and second planar surfaces clamp said curved, elongated object in a vice-like grip.

29. The device according to claim 28 wherein said second planar surface defines the proximal end of a distally curved cap portion.

30. The device according to claim 28 wherein said longitudinal opening in said distal end of said shaft comprises a first portion adapted to allow said hook means to be retracted into and to project from said distal end of said shaft, and a second portion extending transversely across said shaft, said second portion having a longitudinal depth less than the transverse thickness of at least the majority of said curved, elongated object along its length and a contour adapted to receive the curvature of said object in the plane of its arc.

* * * * *